Figure 1A:
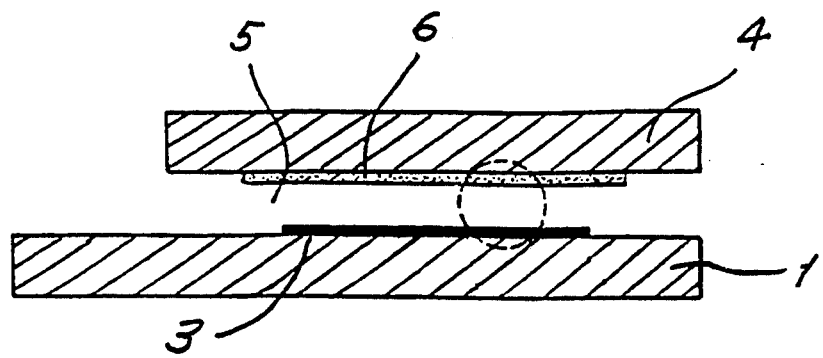
Figure 1B:
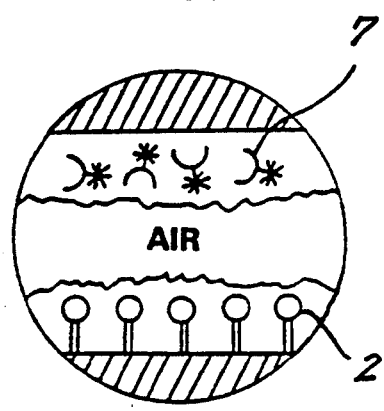

United States Patent
Robinson et al.

[11] Patent Number: 5,356,780
[45] Date of Patent: Oct. 18, 1994

[54] DETERMINIATION OF SUBSTRATE OF COENZYME REQUIRING ENZYME

[75] Inventors: Grenville A. Robinson, London, United Kingdom; John G. Hurrell, Carmel, Ind.

[73] Assignee: Applied Research Systems Holding N.V., Netherlands

[21] Appl. No.: 30,151

[22] PCT Filed: Oct. 14, 1991

[86] PCT No.: PCT/GB91/01781
§ 371 Date: Mar. 17, 1993
§ 102(e) Date: Mar. 17, 1993

[87] PCT Pub. No.: WO92/07266
PCT Pub. Date: Apr. 30, 1992

[30] Foreign Application Priority Data

Oct. 15, 1990 [GB] United Kingdom ............... 9022304

[51] Int. Cl.$^5$ .................. C12Q 1/00; G01N 33/53
[52] U.S. Cl. ................................ 435/7.6; 435/4; 435/7.7; 435/7.72; 435/14; 435/25; 435/26; 435/174; 435/176; 435/288

[58] Field of Search ............... 435/4, 7.6, 7.7, 7.72, 435/, 7.92, 7.93, 14, 25, 26, 174, 176, 288; 356/440; 422/82.11, 58, 68.1

[56] References Cited

U.S. PATENT DOCUMENTS 4,810,635  3/1989  Ledden et al. ............... 435/7.7
4,978,503  12/1990  Shanks et al. ............... 422/58

*Primary Examiner*—Toni R. Scheiner
*Attorney, Agent, or Firm*—Ostrolenk, Faber, Gerb & Soffen

[57] ABSTRACT

The invention relates to a competitive binding assay technique for substances (e.g. small molecules having no antigenic determinant) which can serve as substrates for coenzyme-requiring enzymes. The technique involves contacting a liquid sample with an assay system including (i) a substrate analogue and (ii) a moiety capable of binding specifically to the substrate without catalyzing the conversion of substrate to product. The substrate analogue is a substance capable of binding to said moiety competitively with any of the substrate present in the sample. The presence or amount of the substrate is determined by monitoring the extent to which there are formed or remain complexes between the moiety and substrate or substrate analogue.

10 Claims, 2 Drawing Sheets

DETERMINIATION OF SUBSTRATE OF COENZYME REQUIRING ENZYME

The present invention relates to an assay technique. In particular, it relates to a competitive binding assay technique for substances which can serve as substrates for coenzyme-requiring enzymes.

A large number of substrates of coenzyme-requiring enzymes are small molecules having no antigenic determinant and consequently cannot be assayed by conventional immunoassay techniques. Commonly, such substrates are assayed by monitoring enzymic substrate conversion. Thus, for example, glucose biosensors are known which depend upon the sample to be assayed for glucose being contacted with glucose oxidase (a coenzyme-requiring oxidoreductase enzyme), enzymic conversion of any sample glucose being determined by indirect detection of $H_2O_2$ production or by monitoring electron transfer from the redox centre of the enzyme to a working electrode via an electron transfer mediator. Glucose sensing systems of the latter type are disclosed, for example, in EP-A-076836 and one such biosensor employing disposable electrode strips carrying immobilised glucose oxidase together with an electron transfer mediator is currently made available commercially by MediSense Inc.

Enzyme electrodes for assaying of enzyme substrates are generally considered favourable from the point of view of convenience of use and a low degree of interference, but their lower limit of sensitivity is significantly higher than for known immunosensors for antigenic species owing to the kinetics of enzymic substrate conversion. Thus, whereas immunosensors commonly cover a concentration range of 1 nM to 0.1 mM, enzyme electrodes are typically only of use in assaying substrate concentrations in the range 10 $\mu$M to 1M.

Fibre-optic biosensors for glucose are also known which depend upon competitive binding of sample glucose and fluorescently-labelled dextran to the lectin concanavalin A [Schultz et al, Diabetes Care 5, 245–253 (1982); Anal. Chem. 58, 766A–770A (1986)]. Analogous fibre-optic biosensors for non-haptenic small molecules other than lectin-binding sugars are, however, not known.

The present invention now provides a competitive binding assay technique which is applicable not only to glucose, but also inter alia to any other substrate of a coenzyme-requiring enzyme for which an apoenzyme binding protein with no functional coenzyme component can be obtained.

Thus, according to one aspect of the invention, there is provided a method of assaying within a liquid sample a substance capable of serving as a substrate for a coenzyme-requiring enzyme which method comprises contacting the said sample with an assay system including (i) a substrate analogue and (ii) a moiety capable of binding specifically to the substrate without catalysing the conversion of the substrate (the said substrate analogue being a substance capable of binding to the said moiety competitively with any of the said substrate present in the sample), and determining the presence or amount of the said substrate by monitoring the extent to which there are formed or remain complexes between the said moiety and substrate analogue and/or substrate respectively.

The moiety capable of binding specifically to the substrate without catalysing its conversion will hereinafter be referred to, for brevity's sake, as a specific binding partner. It is to be understood that, at commencement of an assay according to the above method, the specific binding partner and the substrate analogue may be either separate components (the standard format of a competitive assay) or already mutually bound (the format of a displacement competitive assay).

In a preferred embodiment of the invention, the specific binding partner is an appropriate apoenzyme in the absence of its functional coenzyme required for catalytic activity. Accordingly, the invention will be described hereinafter with particular reference to this preferred embodiment.

Other appropriate specific binding partners for use in the method of the invention include partly denatured enzymes (i.e. enzymes which have been appropriately deactivated by partial denaturation under controlled conditions); deactivated "artificial enzymes" such as deactivated cyclodextrins; deactivated enzymes; and genetically engineered deactivated enzymes. Deactivated enzymes (or "artificial enzymes") include enzymes (or "artificial enzymes") the catalytic activity of which has been effectively removed by the addition, either in advance of or simultaneously with introduction of the analyte substrate into the assay, of a suitable deactivating reagent: e.g. the catalytic activity of certain metalloenzymes may be quenched by the addition of EDTA.

It will be appreciated that assays according to the invention may be either qualitative or quantitative.

Monitoring of the proportion of the specific binding partner component complexed with substrate analogue can be achieved by a technique selected from any of the wide variety of known techniques for monitoring competitive binding of an analyte ligand and ligand analogue to a single receptor. Thus, an assay system according to the present invention may, for example, be in the form of an electrochemical, optical, piezoelectric or fibre-optic biosensor. According to one possibility, one of the assay components (i) and (ii) as defined hereinbefore is immobilized on a solid support, and the other of components (i) and (ii) carries a detectable label. For example, a fluorescent label may comprise fluorescein isothiocynate (FITC), whilst an optical sensor may comprise as the solid support an optical waveguide. Moreover, a competitive assay of the present invention, by virtue of the fact that it is analogous to a competitive immunoassay, combines a high degree of specificity with improved sensitivity over enzyme electrode sensors.

It will be appreciated that the apoenzyme component for a preferred assay of the present invention need not be a complete apoenzyme of a coenzyme-requiring enzyme, but may be any portion of the proteineous structure of such an enzyme which retains a functional substrate binding site. Generally, however, it will be found preferable to employ a complete apoenzyme stripped of its normally associated coenzyme partner. Methods for preparation of apoenzymes free of coenzyme are known. See, for example, Methods in Enzymology, 92,415ff-(1983).

The apoenzyme component for an assay of the present invention may, for example, be derived from any of the oxidoreductase enzymes which require a coenzyme for electron transfer at the redox centre of the working enzyme. Thus, examples of particularly preferred assays of the present invention include those employing an apoenzyme component of an oxidoreductase enzyme selected from alcohol dehydrogenase, cholesterol oxidase, lactic acid dehydrogenase and pyruvate dehydrogenase, which may find clinical application in detecting abnormal blood levels of alcohol, cholesterol, lactic acid and pyruvate respectively. More particularly preferred are competitive assays according to the present invention for assay of glucose employing the apoenzyme of glucose oxidase (GOX).

It should be understood that the substrate analogue for an assay of the present invention will be either a (natural or synthetic) species specific for the same binding site of the specific binding partner as the analyte substrate, or a pre-determined quantity of that substrate. Thus, for example in the case of a glucose competitive assay of the present invention, the substrate analogue may, for example, be a pre-determined quantity of glucose itself or dextran (a glucose polymer).

Figure 1D:
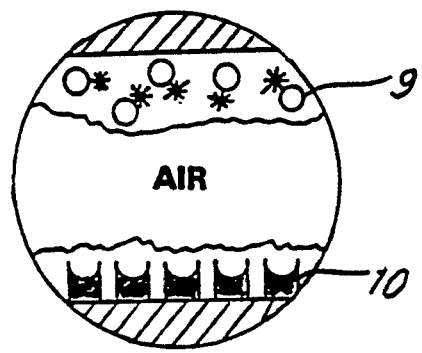
Figure 1C:
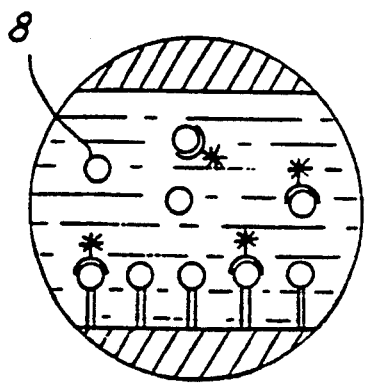
Figure 1E:
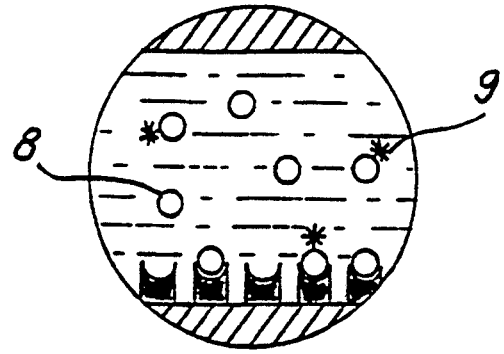
Figure 2:
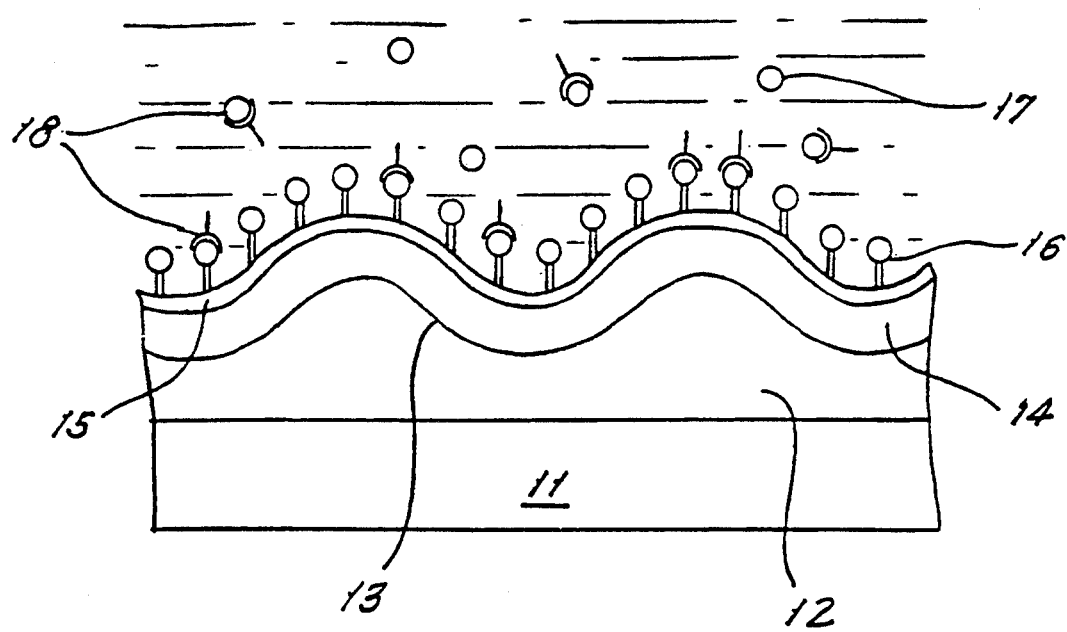
Figure 3:
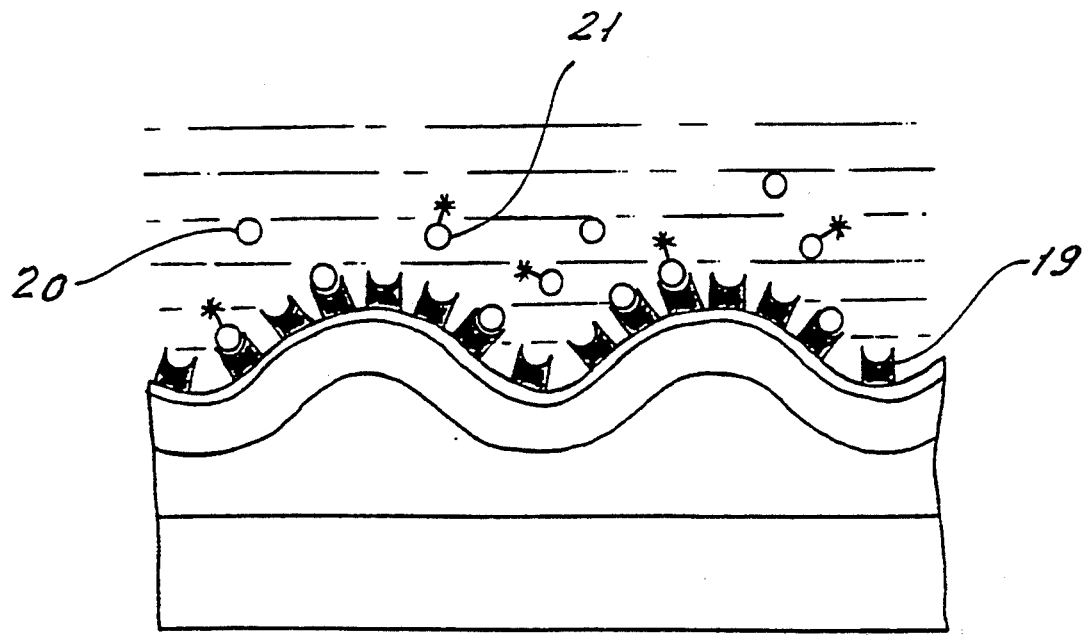

Four especially preferred assay systems according to the present invention employing two different optical techniques for monitoring apoenzyme-substrate versus apoenzyme-substrate analogue complex formation are hereinafter described in more detail with reference to the accompanying figures wherein:

FIGS. 1a, 1b, 1c, 1d and 1e schematically illustrate in cross-section capillary-fill assay systems employing a fluorescently-labelled reagent, fluorescence capillary fill devices (FCFD's), and FIGS. 2 and 3 schematically illustrate assays of the present invention reliant on the optical phenomenon of surface plasmon resonance.

Referring to FIGS. 1(a) and (b), the capillary fill assay system therein shown is a single sample, non-rechargeable assay system comprising the following plate components:

(i) a first plate 1 having immobilized at its inner surface the substrate analogue 2 as a layer 3 of solid phase reagent retaining ability to bind to the chosen apoenzyme component; and (ii) a second plate 4 separated from the said first plate by a capillary cavity 5 and having coated at its inner surface a layer 6 comprising a fluorescently-labelled apoenzyme component 7 in a soluble, releasable form; e.g. where the proposed analyte is glucose, component 7 may be GOX-apoenzyme labelled with a fluorophore such as, for example, fluorescein isothiocyanate (FITC).

At least the said first capillary plate 1 of such a device (hereinafter referred to as an apoenzyme-FCFD) is capable of acting as an optical waveguide.

The manner of performance of an assay using a device of this type is similar to that of known immunosensors of the fluorescence capillary fill device type operating according to the competitive immunoassay mode. See Badley et al., Phil. Trans. R. Soc. Lond. B 316, 143–160 (1987). Thus, an assay is commenced by allowing the liquid sample, e.g. a blood sample, to be drawn into the capillary cavity 5 with consequent solubilization of the labelled apoenzyme component 7 from its initial bound state (see FIG. c). Following equilibration of analyte substrate 8 versus substrate analogue 2 binding to the apoenzyme component 7, completion of the assay depends upon optical excitation of the label and determination of the fluorescent light intensity at a particular angle relative to the plane of the complex-carrying plate, the photodetector position being such that only fluorescent light arising from label bound to this plate is detected. Preferably, where it is desired to carry out a quantitative assay, this light intensity measurement will be expressed as a ratio with a second photodetector reading at a different angle relative to the plane of the same optical waveguide plate, this second angle being selected such that soluble label fluorescence is observed. Methods of optical analysis suitable for use in conjunction with the invention are described in more detail in, for example, EP-A-170376.

As shown in FIGS. 1(d) and (e), the fluorescently-labelled apoenzyme component in an apoenzyme-FCFD device as described above may be substituted by fluorescently-labelled substrate analogue 9 in which case an appropriate unlabelled apoenzyme component 10 capable of binding both the proposed analyte substrate 8 and the labelled substrate analogue 9 will be immobilized on the optical waveguide base plate utilized for photodetector readings. Thus, for example, in the case of an apoenzyme-FCFD of this alternative form adapted for glucose sensing and employing as the solid phase apoenzyme reagent GOX stripped of its coenzyme, the fluorescently-labelled substrate analogue may conveniently be a fluorescently-labelled dextran, e.g. FITC-dextran.

Construction of apoenzyme-FCFD devices can be achieved via initial formation of larger coated plates in analogous manner to the conventional method for the construction of FCFD immunosensors.

Methods of fabricating FCFD's are described in detail in EP-A-171148.

Substrate analogues (for example, dextran in a glucose assay) may be immobilised onto the base plate by coupling the substrate analogue to a suitable protein (e.g. bovine serum albumin, keyhole limpet haemocyanin, poly-L-lysine) and then binding this to the base plate using conventional protein immobilisation chemistry. Apoenzymes may be immobilised by analogous methods.

The known surface plasmon resonance (SPR) technique for carrying out the determination step of a competitive immunoassay (see, for example, EP-A-0276142) may also be favourably applied to monitoring substrate versus substrate analogue binding to an apoenzyme component thereby obviating the need for a measurable label. Devices suitable for use in connection with SPR techniques are described in, for example, EP-A-353937. Thus, as illustrated by FIGS. 2 and 3, SPR-assays according to the present invention may employ either the apoenzyme component or the substrate analogue immobilized on an optical structure capable of exhibiting an SPR effect, e.g. a metallised diffraction grating.

Referring to FIG. 2, a suitable optical structure comprises a substrate 11 carrying a layer 12 of a suitable material (e.g. polyester or polycarbonate) possessing a pre-formed surface relief profile 13. The active surface of the structure comprises a layer 14 of metal (e.g. silver) which conforms at its upper surface to relief profile 13. This layer may be covered by a passive film 15 (e.g. silicon dioxide) which also conforms to profile 13. A monolayer of substrate analogue molecules 16 is bound to the film 15 and is thereby immobilised. During the assay, analyte substrate molecules 17 compete with bound substrate analogue molecules 16 to form complexes 18 with molecules of the apoenzyme component. In FIG. 3, molecules of an apoenzyme component 19 are immobilized, and during the assay analyte substrate 20 and labelled substrate analogue 21 compete for binding to the apoenzyme 19.

It may be found necessary or desirable for the member of the apoenzyme component/substrate analogue pairing which is not immobilized on the optical structure to be bound to an entity to increase its optical thickness enhancing effect upon complex formation. Suitable methods for this purpose are described in the aforementioned published European patent application 0276142 and include binding to polystyrene latex or to a high refractive index material such as glass beads. The sample and soluble reagent may be contacted with the reagent-bearing optical structure either simultaneously or sequentially and the assay completed by observance of the rate or extent to which the surface plasmon resonance effect of the optical structure is changed.

According to a further aspect of the present invention, there is provided a sensor for use in carrying out an assay of the present invention having one of the substrate analogue and an appropriate specific-binding partner immobilized on a solid support to provide a solid phase reagent, the said solid support being adapted to permit monitoring of analyte substrate versus substrate analogue binding to the said specific binding partner.

The said solid support may be an optical structure capable of exhibiting an SPR effect.

A sensor of the invention may be in the form of a specifically reactive sample-collecting and testing device possessing a cavity or cavities each having a dimension small enough to enable sample liquid to be drawn into the cavity by capillary action, and wherein either the substrate analogue or an appropriate specific binding partner is immobilised on at least one part of a wall of said cavity. In this embodiment, said wall of the cavity acts as the solid support described hereinbefore.

In addition to apoenzyme-FCFDs and optical structures bearing an immobilized reagent for an SPR assay of the present invention, such devices include, for example, a working electrode having immobilized thereon an appropriate specific binding partner (for example an apoenzyme component devoid of functional coenzyme); and fibre-optic and piezoelectric biosensors for performing an assay of the present invention and incorporating an appropriate immobilized specific binding partner, for example a non-catalytic apoenzyme component.

According to a still further aspect of the invention, there is provided a kit for use in a method of assay as described hereinbefore. The kit comprises (i) a substrate analogue and (ii) a moiety capable of binding specifically to the substrate without catalysing the conversion of the substrate.

We claim:

1. A method of assaying within a liquid sample a substrate for a coenzyme-requiring enzyme which method comprises contacting the sample with an assay system including (i) a substrate analogue and (ii) a moiety which specifically binds the substrate without catalyzing the conversion of the substrate; the substrate analogue being a substance which competes with the substrate for binding to the moiety, and determining the presence or amount of the substrate by monitoring the extent to which there are formed or remain complexes between the moiety and at least one of the substrate analogue and the substrate; wherein the moiety is selected from the group consisting of an apoenzyme which is not bound to its functional coenzyme, a partly denatured enzyme, a deactivated enzyme, a genetically engineered deactivated enzyme and a deactivated artificial enzyme.

2. A method as claimed in claim 1 wherein component (ii) comprises an apoenzyme which is not bound to its functional coenzyme.

3. A method as claimed in claim 2 wherein the apoenzyme is the apoenzyme of an oxidoreductase enzyme selected from the group consisting of alcohol dehydrogenase, cholesterol oxidase, lactic acid dehydrogenase and pyruvate dehydrogenase.

4. A method as claimed in claim 2 wherein the apoenzyme is the apoenzyme of glucose oxidase.

5. A method as claimed in claim 1 wherein component (ii) comprises a partly denatured enzyme.

6. A method as claimed in claim 1 wherein component (ii) comprises a genetically engineered deactivated enzyme.

7. A method as claimed in claim 1 wherein one of components (i) and (ii) is immobilised on a solid support, and the other of components (i) and (ii) carries a detectable label.

8. A method as claimed in claim 7 wherein the solid support is an optical waveguide and the detectable label is a fluorophore.

9. A method as claimed in claim 7, wherein the support is a part of a fluorescence capillary fill device and said determining is effected by detecting fluorescence.

10. A method as claimed in claim 1, wherein said determining comprises an optical technique employing surface plasmon resonance.

* * * * *